United States Patent [19]

Stoy et al.

[11] Patent Number: 5,217,026

[45] Date of Patent: Jun. 8, 1993

[54] GUIDEWIRES WITH LUBRICIOUS SURFACE AND METHOD OF THEIR PRODUCTION

[75] Inventors: George P. Stoy, South Brunswick Township, Middlesex County; Vladimir A. Stoy, Princeton, both of N.J.

[73] Assignee: Kingston Technologies, Inc., Dayton, N.J.

[21] Appl. No.: 864,472

[22] Filed: Apr. 6, 1992

[51] Int. Cl.⁵ ............... A61M 25/00; A61M 5/00; C08F 20/44

[52] U.S. Cl. .................. 128/772; 128/657; 604/170; 604/264; 524/916; 525/329.1; 525/329.2; 427/336

[58] Field of Search .......... 128/772, 657, 658; 604/280, 264, 170; 264/41, 173, 177.18, 182; 427/208.4, 337, 336; 523/113; 524/916; 525/329.1, 329.2, 324.3; 428/424.7

[56] References Cited

U.S. PATENT DOCUMENTS

| | | | |
|---|---|---|---|
| 3,566,874 | 3/1971 | Shepherd et al. | 604/265 |
| 3,695,921 | 10/1972 | Shepherd et al. | 427/2 |
| 3,861,396 | 1/1975 | Vaillancourt et al. | |
| 3,862,452 | 1/1975 | Wichterle et al. | |
| 3,975,350 | 8/1976 | Hudgin et al. | 524/108 |
| 3,987,497 | 10/1976 | Stoy et al. | 427/171 |
| 4,026,296 | 5/1977 | Stoy et al. | |
| 4,100,309 | 7/1978 | Micklus et al. | 427/2 |
| 4,119,094 | 10/1978 | Micklus et al. | |
| 4,183,884 | 1/1980 | Wichterle et al. | 264/41 |
| 4,255,550 | 3/1981 | Gould | 528/44 |
| 4,527,293 | 7/1985 | Eckstein et al. | 623/12 |
| 4,545,390 | 10/1985 | Leary | 128/772 |
| 4,579,127 | 4/1986 | Haacke | 128/772 |
| 4,668,221 | 5/1987 | Luther | 604/166 |
| 4,743,629 | 5/1988 | Karakelle et al. | 521/175 |
| 4,798,593 | 1/1989 | Iwatschenko | 604/164 |
| 4,811,743 | 3/1989 | Stevens | 128/772 |
| 4,815,478 | 3/1989 | Buchbinder et al. | 128/772 |
| 4,826,485 | 5/1989 | Johnson | 604/170 |
| 4,834,709 | 5/1989 | Banning et al. | 604/170 |
| 4,867,173 | 9/1989 | Leoni | 128/772 |
| 4,884,579 | 12/1989 | Engelson | 128/772 |
| 4,895,168 | 1/1990 | Machek | 128/772 |
| 4,925,445 | 5/1990 | Sakamoto et al. | 604/95 |
| 4,943,618 | 7/1990 | Stoy et al. | 525/329.1 |
| 5,015,238 | 5/1991 | Solomon et al. | 604/164 |

Primary Examiner—Stephen C. Pellegrino
Assistant Examiner—Gary Jackson
Attorney, Agent, or Firm—Kenneth P. Glynn

[57] ABSTRACT

The present invention guidewire involves an elongated, non-hydrogel core element forming an inner part of the device, and an integral outside tubular layer of elastomeric hydrogel ("hydrogel sleeve"). This outer hydrogel layer has unique physical characteristics. They are (a) Gradient of chemical composition with increasing concentration of polar groups in the outward direction away from the core element; (b) Gradient of swelling in contact with water with water content increasing in the outward direction away from the core element; (c) Compressive stress in the outer hydrophilic layer causing the hydrogel in that layer to swell to a water content lower than its equilibrium value in a free-swelling state; and, optionally, (d) Inward-directed radial stress pushing the outside hydrogel layer constantly against the inner core element. The present invention also involves the methods of making these guidewires, including melt extrusion directly onto the core element, coagulation from solution, in situ hydrogel polymer formation, and tubing extrusion followed by consequent shrink-fit over the core.

31 Claims, 6 Drawing Sheets

GUIDEWIRES WITH LUBRICIOUS SURFACE AND METHOD OF THEIR PRODUCTION

BACKGROUND OF THE INVENTION

Guidewires are devices designed to facilitate insertion and placement of various tubular instruments such as catheters, stents, drains, cystoscopes, dilators and other items designed for penetration into various organs or body cavities to perform delivery or withdrawal of fluids, securing patency or access, removal of tissues for diagnostics or surgery, facilitating entry of other devices, etc.

In some procedures, guidewires are typically placed within the body at the desired location in advance, creating a convenient pathway for tubular instruments which are slid into their proper place over it. In other procedures, guidewires are inserted into the desired location together with the tubular instrument or device, e.g. a catheter, providing temporary stiffening needed for the insertion. Once the tubular instrument is in place, the guidewire may be removed and the instrument used for its primary purpose.

Guidewires are of various configurations, made from various materials and are made for various purposes. Their various kinds are sometimes also called Seldinger wires, introducers, mandrels, stylets etc. In the present specification, all such insertion devices for carrying tubular instruments to a desired body location are generally referred to as "guidewires".

In spite of their diverse shapes, sizes and uses, all guidewires devices have several problems in common (albeit, in various extent).

Each of these devices is required to penetrate through tight passages, which are often long and tortuous. This penetration is hindered by friction. The friction complicates the device placement, and may even cause injury to certain surfaces (e.g. tracheal, urethral or vascular wall). Therefore, the outer surfaces have to have low friction against contacting surfaces (e.g. vascular walls, inner walls of catheters or other instruments).

The low friction can be to some extent achieved by creating smooth, high quality surfaces (e.g. polished stainless steel, smooth plastic coatings, etc.). Since this is not always possible or sufficient, guidewires are often equipped with surface layers of various low-friction materials.

One such material widely used is poly(tetrafluoroethylene) (often known as TEFLON ®) or similar fluoropolymers. It is used mostly on metallic guide-wires, either as a coating or as a sleeve pulled over the device.

For instance, U.S. Pat. No. 4,579,127 of Claus Haacke directed to a mandrel for hose type catheters and body probes, describes guidewires made from wound metal wires equipped with thin plastic coatings which follow the contours of the wire surfaces.

As another example, U.S. Pat. No. 4,811,743 of Robert C. Stevens describes a catheter guidewire consisting of a metal flexible core with spherical tip surrounded by sheath of tightly wound wire. The outside sheath surface is provided with a thin (<0.001") Teflon ® coating. Also, U.S. Pat. No. 4,826,485 of Theodore D. Johnson relates to a device for guiding tubings and describes a stylet for introducing, for example, gastric feeding tubes. The cable is made from metal or plastic wire, which forms the central portion of the stylet, which may be coated with an inert polymeric material such as medical grade Teflon ®. The thickness of the coating is typically 0.002–0.004". Likewise, U.S. Pat. No. 4,834,709 of Robert D. Banning et al describes a preformable silicone catheter with a malleable stylet, comprising a malleable wire core and a plastic covering made of a polypropylene (preferred), polyethylene, Teflon ®, etc. The covering can be formed either as a coating, or from a pre-extruded plastic tubing which has larger lumen than the outer diameter of the wire so that it can be readily inserted.

Also, U.S. Pat. No. 4,867,173 of Gianni Leoni is directed to a steerable guidewire and describes a small-diameter guidewire for percutaneous translumenal coronary angioplasty (PTCA). The main core wire is said to be coated with a frictionless material such as Teflon ®. Another U.S. Pat. No. 4,545,390, describes a guidewire with a Teflon ®-coated main core wire.

Sometimes the plastic cover or coating has primary purpose of providing additional safety. For instance, U.S. Pat. No. 4,925,445 of Hidetoshi Sakamoto et al: "Guide wire for catheters" describes guidewire made from "super-elastic" memory titanium nickel or other metal alloys. It is provided with a plastic coating to increase its resistance against buckling. The coating can be made from an elastomeric or a composite material of a synthetic resin material including polyethylene, polyvinyl chloride, TEFLON ®, silicone rubber, etc.

U.S. Pat. No. 4,895,168 of James E. Machek entitled "Guidewire with movable core and external tubular safety cover" describes a guidewire with a wound wire casing covered by a plastic safety cover which is supposed to retain fragments of broken wire. This safety cover is preferably from heat-shrinkable TEFLON ® tubing.

U.S. Pat. No. 4,884,579 of Erik T. Engelson: "Catheter Guide Wire" describes a guidewire with three sections of progressively decreasing rigidity. The central section has surface which is more lubricous than surfaces of adjacent proximal and distal sections. The intermediate section comprises a wirecore segment with flexible polymer covering which encases the intermediate core segment. The covering polymeric material provides appropriate flexibility to this section. The flexible polymer covering can be applied by spraying or dipping, or by a pre-formed tube which can be attached by heat shrinking over the core wire. This section has also low friction polymer surface. This can be achieved by using a covering made from a polymer which has a low friction in itself, such as TEFLON ®.

Alternatively, this polymer covering can be provided with a surface coating of a highly hydrophilic, low friction polymer, such as polyvinylpyrrolidine, polyethyleneoxide or poly(2-HEMA). Such a surface coating can be applied by spraying or dipping according to known methods.

This last example suggests the use of hydrophilic polymer surface coatings which have various advantages. For instance, hydrophilic coatings typically have lower wet friction than, e.g. Teflon ®. They have lesser adhesion to tissue, to thrombus or to clot so that they are less prone to clogging, sticking to the wound, etc. Still another advantage is that the hydrophilic polymer layers can be used as a carrier for various water-soluble drugs, such as antibiotics.

Because of these advantages, hydrogel-coated surgical tubular devices are often suggested in the prior art. (For instance: U.S. Pat. No. 3,566,874 Francis E.

Gould, Thomas H. Shepard: Catheter, U.S. Pat. No. 3,862,452 Otto Wichterle et al: Hydrogel Substitutes for Tubular Somatic Organs, U.S. Pat. No. 3,861,396 Vincent L. Vaillancourt et al: Drainage Tube, U.S. Pat. No. 4,026,296 Artur Stoy et al: Hydrophilic Surgical Tubular Device, U.S. Pat. No. 4,527,293 Eugene C. Eckstein et al: Hydrogel Surface of Urological Prothesis, U.S. Pat. No. 5,015,238 Donald D. Solomon et al: Expandable obturator and catheter assembly including same, to name only some.)

To this purpose, various hydrogel coating systems have been developed, based on polymerizable acrylic coatings (e.g. U.S. Pat. No. 3,695,921 Francis E. Gould, Thomas H. Shepard: Method of coating a catheter), on hydrophilic polyurethanes (e.g. U.S. Pat. No. 3,975,350 Donald E. Hudgin and Edgar A. Blair: Hydrophilic or Hydrogel Carrier Systems such as Coatings, Body Implants and other Articles), crosslinked poly(vinylpyrrolidine) (e.g. in U.S. Pat. No. 4,100,309 Michael J. Miclus et al: Coated substrate having a low coefficient of friction hydrophilic coating and a method of making the same; and U.S. Pat. No. 4,119,094 Michael J. Miclus et al: Coated substrate having a low coefficient of friction hydrophilic coating and a method of making the same etc.).

Such hydrophilic coatings can be applied also to guidewires. For instance, U.S. Pat. No. 4,798,593 of Peter Iwatschenko: Stiffening of probes describes mandrels for catheters etc. consisting of a wire element with coating of a biocompatible material of which at least the surface in hydrophilic. The coating may be applied by dipping or spraying. A specific hydrophilic polymer mentioned is gelatin softened, e.g., by glycerol.

In another example, U.S. Pat. No. 4,815,478 Maurice Buchbinder et al: "Steerable Guidewire with deflectable tip" describes a steerable guidewire consisting of a tubing (preferably flexible metal tubing) which provides for steering of a deflection wire, and a spring coil distal end. It is mentioned that it is advantageous to cover whole length of the guidewire, preferably including the tip, with a lubricious coating made from polymer such as Teflon ® or a hydrogel.

The prior art hydrophilic coatings have certain specific problems:

1) There is often a problem to achieve a secure adhesion of the swellable hydrogel layer to the non-swellable substrates, such as crystalline hydrophobic polymer (TEFLON ®, polyolefin), or metal substrates. The main source of this problem is the volume change due to the swelling and the sharp transition between the swellable and non-swellable layer. A considerable shear stress can be thus generated in the interface which tends to separate the two materials. This may lead to delamination, peeling off and shedding of the resulting debris;

2) Difficult control of the surface thickness due to the swelling characteristics of the polymer;

3) Weakness in the polymer skin. The highly hydrophilic layers are soft and poorly resistant to scratching, abrasion or other mechanical damage. The denuded hydrophobic substrate can cause thrombus formation or other problems;

4) Increased production cost, particularly because the coating is applied to an otherwise finished, final device. Coating defects thus generate very expensive off-grades.

The present invention overcomes the above problems utilizing a heretofore untaught and unobvious device and method of production.

SUMMARY OF THE INVENTION

The present invention guidewire involves an elongated, non-hydrogel core element forming an inner part of the device, and an integral outside tubular layer of elastomeric hydrogel ("hydrogel sleeve"). This outer hydrogel layer has unique physical characteristics. They are (a) Gradient of chemical composition with increasing concentration of polar groups in the outward direction away from the core element; (b) Gradient of swelling in contact with water with water content increasing in the outward direction away from the core element; (c) Compressive stress in the outer hydrophilic layer causing the hydrogel in that layer to swell to a water content lower than its equilibrium value in a free-swelling state; and, optionally, (d) Inward-directed radial stress pushing the outside hydrogel layer constantly against the inner core element. The present invention also involves the methods of making these guidewires, including melt extrusion directly onto the core element, coagulation from solution, in situ hydrogel polymer formation, and tubing extrusion followed by consequent shrink-fit over the core.

BRIEF DESCRIPTION OF THE DRAWINGS

The present invention is more fully appreciated when the specification herein is taken in conjunction with the appended drawings wherein.

DETAILED DESCRIPTION OF THE INVENTION

The present invention is directed to a guidewire with a core element and a tubular layer of elastomeric hydrogel with specified unique physical characteristics.

It is an object of the present invention to provide for guidewires and their methods of production which overcome surface thickness control problems, which are highly resistant to scratching, abrasion and mechanical damage, to decreased production costs and to increased adhesion between the lubricious coating and the core element.

The core element may be a single wire or a braided assembly of multiple wires. It may be a very simple cylindrical element, or it may have a variable cross section or even be a very complicated structure (e.g., a steerable guidewire, guidewire with segments of various flexibility, etc). It may be made of a metal, of a rigid plastic, carbon fibers, glass, ceramics or of a combination of various materials. The core element must be of sufficient rigidity so as to be insertable into a body. In general, such core elements are at least about 0.002 inches in diameter and typically about 0.006 inches to about 0.050 inches in diameter.

The outside elastomeric hydrogel may have various chemical compositions. It may be covalently cross-linked acrylic hydrogel, such as poly(2-HEMA) or other well known compositions based on hydrophilic derivatives of acrylic or methacrylic acid. It may be also based on crosslinked hydrophylic polyvinylic compounds, such as poly(vinylalcohol) and various copolymers thereof.

Particularly advantageous for this application are thermoplastic hydrogels which may be processed into tubular shapes by melt extrusion, such as various hydrophilic polyurethanes (see, for instance, U.S. Pat. No. 4,743,629) or hydrogels derived from modified polyacrylonitrile (see e.g. U.S. Pat. No. 4,943,618). Similar hydrogel tubes can be also produced by coagulation of solutions of certain hydrogels in organic solvents (see e.g. U.S. Pat. No. 4,183,884.

The outer hydrogel layer has gradient of chemical composition and swelling such that use substantially more hydrophobic on its inner surface contacting the said core element than it is on its outside surface. The hydrogel close to the outer surface has preferably high concentration of ionic groups, such as carboxylic, sulfonic, or sulfate groups. The typically between 10% and 75% of the wall thickness.

This gradient of composition and properties are achievable by after-treatment of a basic hydrogel tube. The tubular hydrogel with a low water content (i.e., composition corresponding to the inner hydrogel surface) is reacted with a core-agent introducing hydrophilic groups into the hydrogel structure. If the diffusion rate and reaction rate are properly balanced, the desired gradient of hydrophilicity is formed. Such surface hydrophilization reactions are well known to those skilled in the art (see e.g. above cited U.S. Pat. No. 4,183,884 and U.S. Pat. No. 4,943,618 as well as Examples).

The outer surface hydrophilization can be hydrogel close to the inner surface has preferably high concentration of hydrophobic or non-polar groups, such as alkyl acrylate or methacrylate groups, nitrile groups, etc.

Consequently, the hydrogel in the inner zone near its inner surface preferably has a water content between about 25% and 50% of water by volume, while the water content near the surface or outer layer is preferably higher than 90% or even higher than 95% of liquid. There is a gradual, smooth transition of composition and water content between the outer and inner surfaces.

The overall thickness of the hydrogel sleeve can vary in broad limits, typically between about 0.001" and about 0.1". The gradient layer is performed on the tube itself, or after it was attached to the core element.

This additional chemical modification creates the gradient of chemical composition and swelling. In addition, it causes the layers with increased hydrophilicity to be compressed, i.e., swelling less in contact with water than a heterogeneous hydrogel of the same composition and structure would. This can be readily demonstrated by peeling off a portion of the outer layer of fully swollen guidewire of the present invention and placing it into an excess of swelling liquid: this hydrogel will expand and imbibe additional water.

The gradiented structure thus formed has several advantages:

1) Its inner surface contacting core element is substantially hydrophobic with relatively high friction so that its safe attachment can be readily achieved;

2) The outermost layer contacting tissue or other devices is extremely hydrated, providing very low friction and adhesion vs contacting surfaces;

3) There is no sharp interface with a shear stress acting toward separation of the layers of different swelling. The stress caused by the different swelling is safely distributed through the structure and effectively eliminated;

4) The surface is highly resistant to mechanical damage since surface defects caused by mechanical damage are self-healing due to the torque stiffness.

This is unique property of these structures and very desirable property for a guidewire.

This radical/tangential stress is achieved by applying the hydrogel sleeve on the core element or at least a portion of it, which has O.D. larger than I.D. of the sleeve. This can be readily achieved by applying the sleeve in state of higher than equilibrium swelling. The swelling is artificially and temporarily increased (e.g., by inflation, action of solvents, etc.), resulting in expansion of the hydrogel and in increasing size of its lumen. Once the sleeve is placed over the mandrel, the swelling is decreased back to its equilibrium value (e.g., by heating, evaporating part of the swelling pressure: removal of any part of the surface decreases pressure limiting the swelling in the adjacent part; the adjacent hydrogel portion thus increases its swelling to fill any gap automatically.

Another attribute of our invention is the inward radical stress in the hydrogel sleeve. Owing to this stress, the sleeve surface copies the contour of the core element, and the sleeve is firmly attached even without any adhesives or other bonding means. The tangential component of this stress stretches and partly orients the polymer in that direction. In case of semicrystalline hydrogels (such as modified polyacrylonitrile hydrogels") such tangential orientation results in selectively increased solvent, etc.), and the sleeve will shrink, encasing the core element firmly.

The inward radial stress can be supplemented and/or replaced by application of appropriate adhesives securing the sleeve to the core. The adhesives may be cyanoacrylates, polyurethanes, epoxides or similar formulations well known to those skilled in the art.

Figure 1:
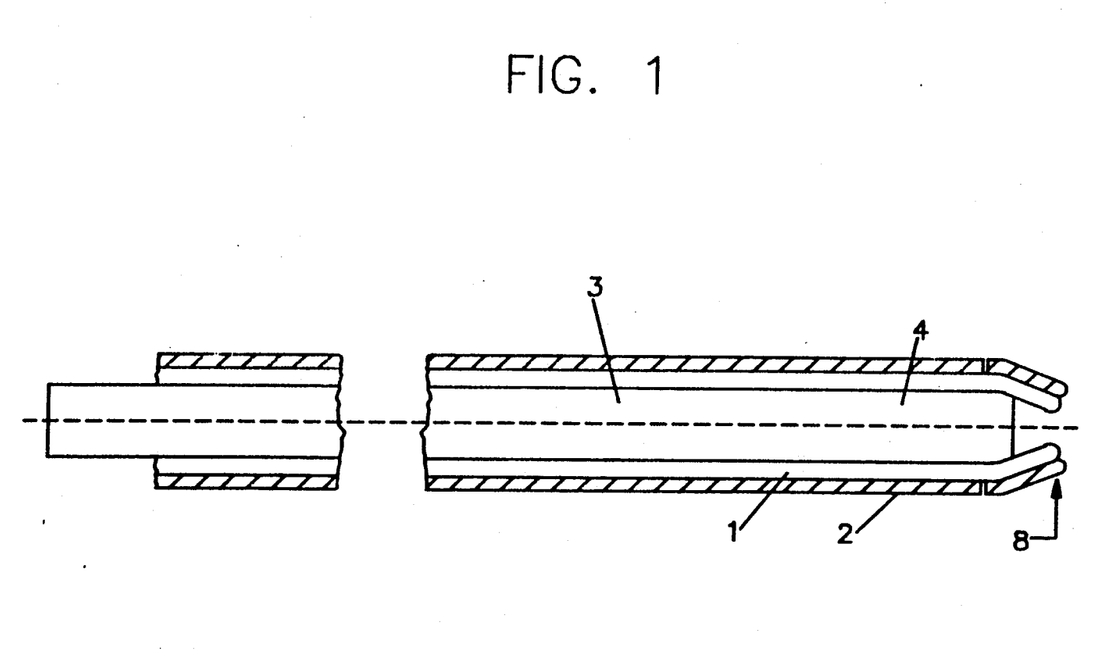
FIG. 1 shows a side view of a present invention guidewire, wherein the hydrogel sleeve with an outer gradiented layer is applied over a metal core.

Referring now to the figures, FIG. 1 shows a side view of a present invention guidewire, wherein the hydrogel sleeve 1 with outer gradiented layer 2 is applied over a metal core 3. Part of the sleeve 1 exceeds core 3 at its distal end 4 forming the soft buffer tip 8 upon hydrogel contraction.

Figure 2:
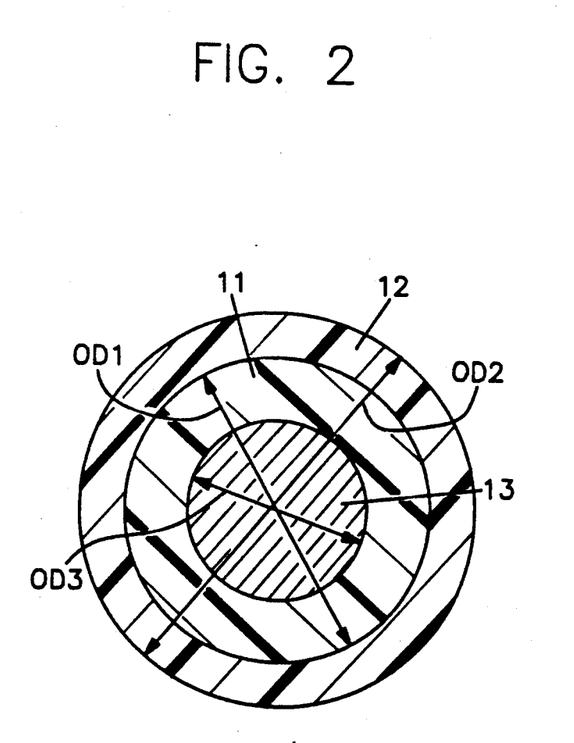
FIG. 2 shows a guidewire cross section of metal core, a hydrogel sleeve and gradiented layer with hydrophilicity increasing in an outward direction.

FIG. 2 shows a guidewire cross section wherein 13 is metal core, 11 is a hydrogel sleeve and 12 is the gradiented layer with hydrophilicity increasing in outward direction. OD1, OD2 and OD3 are outside diameters of the hydrogel sleeve, gradiented layer and the metal core, in accordance with the present invention, respectively.

Figure 3:
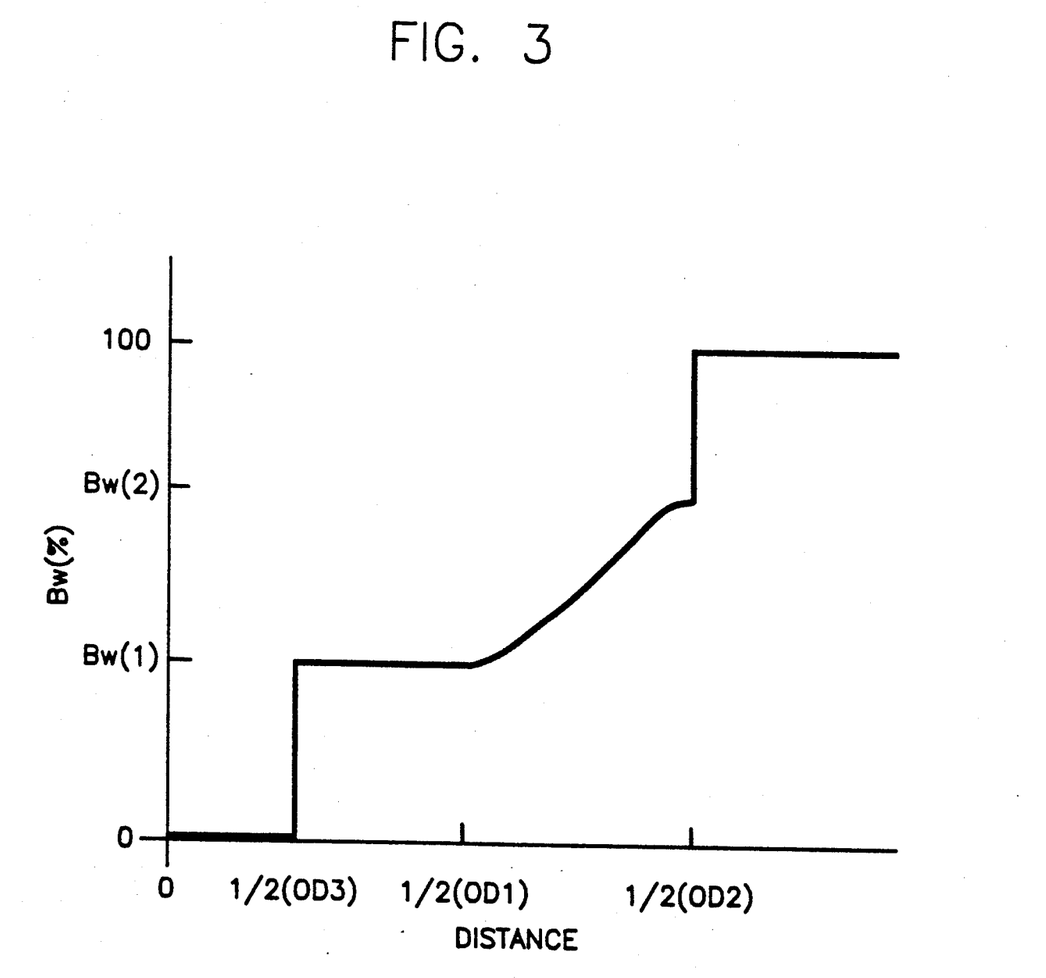
FIG. 3 shows water content as a function of distance from a central core axis of a present invention device.

FIG. 3 shows water content Bw (in wt. %) as function of distance (D) from the central core axis. Bw(1) is the water content in the hydrogel sleeve, Bw(2) is the water content in the outside portion of the gradiented layer. Water content is in contact with excess of water.

Figure 4:
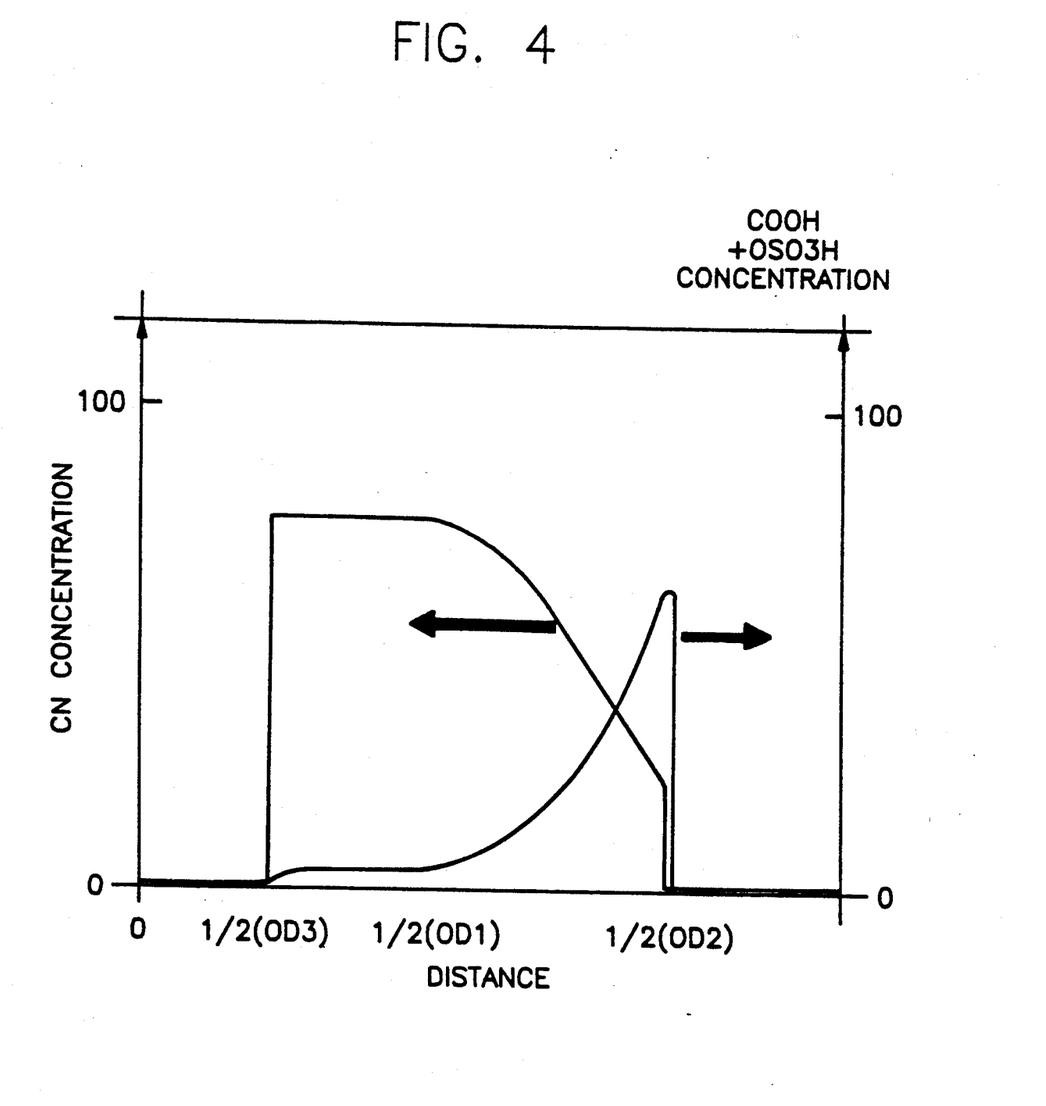
FIG. 4 shows a composition profile of guidewire from FIG. 3 using hydrogel from Example 1.

FIG. 4 shows a composition profile of guidewire from the FIG. 3 using hydrogel from the Example 1. The left axis shows concentration of CN groups, and the right axis shows concentration of anionic groups (in mol % in the polymer). This clearly establishes the composition gradient of the present invention.

Figure 5:
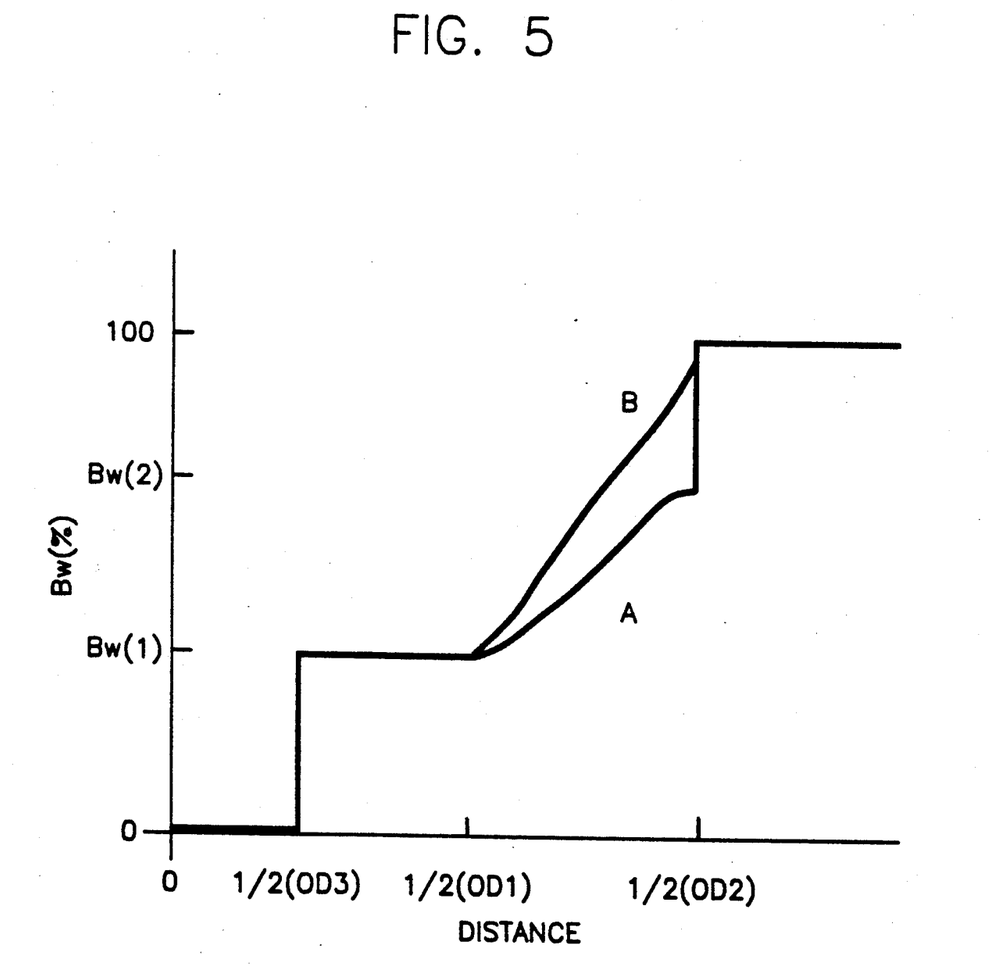
FIG. 5 shows a similar diagram as in FIG. 3 with the curve A corresponding to FIG. 3 and the additional curve B representing free-swelling water content.

FIG. 5 shows similar diagram as FIG. 3 with the curve A corresponding to the FIG. 3 curve and with the additional curve B. The curve B shows water content in a hydrogel of the same chemical composition and structure as the hydrogel in the gradiented layer in the same distance from the axis, just as in FIG. 3, except that it corresponds to free-swelling water content of the layers as in the sleeve as if they were detached from the adjacent layers with the lower and the higher hydrophilicity, respectively. This value is measured, for example, by gradually peeling off thin layers of the sleeve and immersing the material in excess of water.

Figure 6:
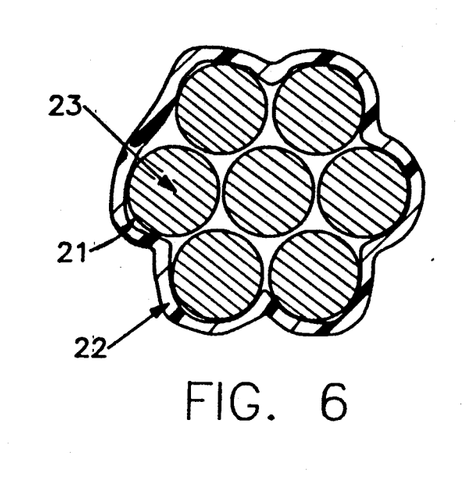
FIG. 6 shows a cross section of guidewire which the core is composed of a multitude of wound wires; and, FIG. 7 shows guidewire assembly from Example 1 where the metal cylindrical core has tapered the distal end, to which there is connected platinum wire coil with a spherical end.

FIG. 6 shows cross section of guidewire which core 23 is composed of a multitude of wound wires. The hydrogel sleeve 21 with the gradiented layer 22 approximates the surface of core 23.

Figure 7:
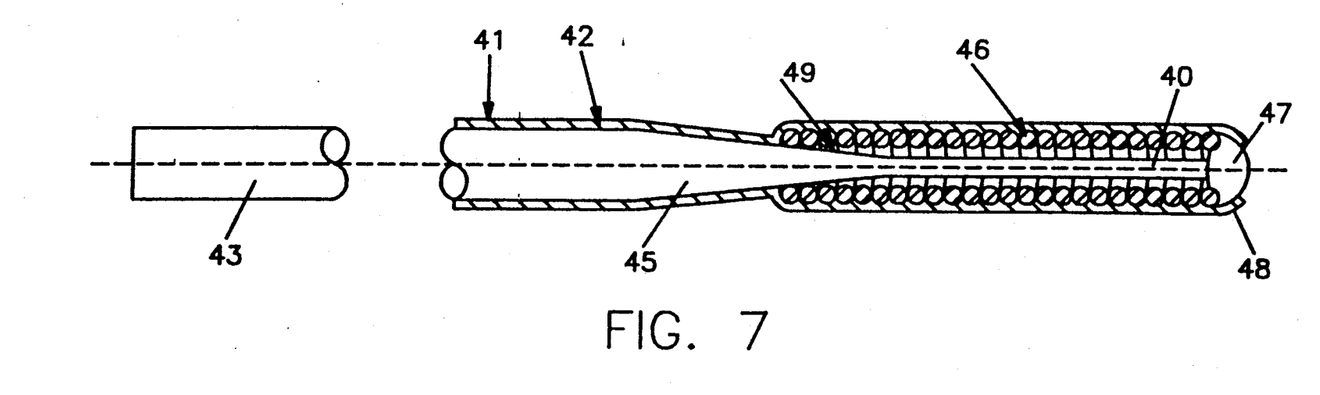

FIG. 7 shows guidewire assembly from Example 1 where the metal cylindrical core 43 has tapered distal end 45, to which there is connected platinum wire coil 46 with spherical end 47. The coil 46 is connected to tapered distal end 45 via solder connection 49. The hydrogel sleeve 41 with surface gradiented layer 42 covers the tapered end 45 and the coil 46. The sleeve forms soft buffer tip 48 at the distal guidewire end 40.

EXAMPLES

Example 1

A hydrogel was prepared by partial acidic heterogeneous hydrolysis of polyacrylonitrile described in U.S. Pat. No. 4,943,618. The hydrolytic reaction was carried out to the conversion of 37%, i.e. the copolymer contained 63 molar % of acrylonitrile units organized in blocks. This polymer was compounded with DMSO which was used as plasticizer for extrusion.

The composition containing 52% of the copolymer and 48% of the DMSO plasticizer was melted and extruded to form a tubing having ID=0.009", OD=0.014".

The DMSO-plasticized tubing wa slid immediately after extrusion over a stainless steel wire tapered from 0.014" to 0.003" in a length of 12" in such a way that the proximal end of the sleeve reached to the tapered part of the core where the diameter was 0.009". The distal end of the sleeve was left 2 inches longer than the metal core.

This assembly was then exposed to a stream of humid air. Due to the moisture pick-up, part of the plasticizer was exuded. The tubing shrank due to the solvent loss. The new ID=0.007" caused tubing to grip the core firmly, providing the adherence of the tubing to the metal core 43. The solvent (in this case DMSO) was then extracted with excess of water, causing further shrinkage of the hydrogel.

The washed hydrogel sleeve was then soaked in a 60% Glycerol in water for 3 days to achieve an equilibrium through the entire hydrogel layer. The assembly was then let to dry on the air for 24 hours to remove most of the water from the hydrogel sleeve.

The outer surface of the sleeve was then modified in the following manner:

The assembly with the glycerol-plasticized hydrogel was dipped at 86° C. for 30 seconds into a bath consisting of 80% of Sulfuric acid and 20% Glycerol. The polymer substrate, bath composition, temperature and time were selected in such a way as to create a gradient of swelling and chemical composition. Sulfuric acid residuals were extracted in water. The washed tubing was soaked again in a 60% glycerol in water for 3 days and let air-dried for 24 hours.

The distal end of the plasticized hydrogel tubing was trimmed and a platinum coil was attached. The coil was made of a 0.001" diameter wire and its overall diameter was 0.014" and its length was 2 inches. It was brazed by a gold brazing compound to the distal end of the stainless steel core.

The resulting cardiology guidewire is depicted in FIG. 7. It consists of a platinum coil distal end 47 for improved radiopacity and safe handling; approximately 10 inches long tapered core portion 45 of the guidewire with the gradiented hydrogel sleeve 41, and the cylindrical wire core 43.

The part of the core 43 which is not covered with the hydrogel sleeve is approximately 5 feet long. The coil 46 and tapered core 45 are connected by solder 49.

The adhesion between the core and the sleeve is due to the inward radial stress in the hydrogel layer.

The chemical surface modification causes creation of extremely slippery surface in the swollen state which is resistant to abrasion, scratching or other mechanical damage.

The reaction of glycerol and sulfuric acid converted nitrile groups into amide and carboxyl groups, thus increasing hydrophilicity of the polymer. At the same time, transesterification reactions crosslinked the hydrophilic layer and introduced highly polar glycerol sulphate groups. The resulting gradient of swelling and composition are schematically shown in FIGS. 3 and 4, respectively.

EXAMPLE 2

Tubing is extruded as in the Example 1, but instead of insertion over the wire, it is surface hydrophilized by-passing through bath consisting of 90% sulfuric acid and 10% of glycerol. The bath temperature is 95° C. and the residence time is 15 to 25 seconds.

The tubing is then washed in water, then in 1% solution of sodium bicarbonate and again in water.

This hydrogel sleeve is slid over the distal platinum coil made in a diameter of 0.008", and was brazed to the stainless steel core prior to the sleeving. The fit is achieved by drying the hydrogel sleeve 41 at temperature 100° C. for 1 hour, and then reswelling the sleeve in 60% glycerol for 3 days. Finally, the guidewire is dried in ambient air for 24 hours.

EXAMPLE 3

Hydrogel tubing was extruded as in Example 1, but the solvent was extracted immediately after the extrusion. Tubing was then soaked in 40% NaSCN in water for 12 hours at room temperature, where its inner diameter increased from 0.007" to 0.018". The tubing was then placed over a stainless steel core 0.010" diameter in its entire length of 6 feet and the solvent extracted in water. The hydrogel sleeve had a tendency to shrink to ID 0.007", so the entire covered part of a guidewire was effectively wrapped in a sleeve. The proximal end of the sleeve was trimmed to the same length as the metal core, but the distal end was left longer of approximately 1 ½ inches, creating a soft, conformable safe tip. The swelling gradient and low friction characteristics of the hydrogel sleeve was achieved as in Example 1.

EXAMPLE 4

The same hydrogel as in Example 1 was extruded directly over a stainless steel wire of 0.010" diameter. Hydrogel layer was 0.003" thick on radius, creating an assembly of 0.016" in diameter. Due to solvent extraction and subsequent hydrogel shrinking, described in Example 1, the resulting diameter of the assembly was 0.014". After the solvent extraction, the continuous sleeved wire was cut to length of approximately 6 feet, the distal tip heated to 100° C. in a boiling water in a length of approximately 2 inches and elongated about 100%, creating a tapered soft distal tip without the metal core. The swelling gradient and low friction characteristics were obtained as is described in Example 1.

EXAMPLE 5

Hydrogel tubing, described in Example 1, but of ID=0.018" and OD=0.023" was extruded and the solvent extracted in water. Tubing was then heated to 95° C. in a water bath and a steel mandrel of 0.025" diameter was forced into a tubing lumen. After the tubing cooled down to a room temperature, the mandrel was removed and the tubing placed over a stainless steel core in its entire length of about 4 feet, leaving the tubing longer of several inches over both the distal and proximal ends. The assembly was then heated to 95° C. in a water bath, causing the hydrogel tubing to shrink, creating a sleeved metal core of 0.025" diameter. The proximal end of the sleeve was trimmed to the length of the metal core and the distal end was left 2 inches longer, creating again, soft safe tip. The low friction characteristics and a swelling gradient was obtained as described in Example 1.

EXAMPLE 6

A solution of 20% of hydrophilic polyurethane, as described in U.S. Pat. No. 4,255,550 in ethanol was prepared.

Stainless steel wire of 0.010" diameter was dipped into the solution at 25° C. and slowly pulled back in a vertical position. The solvent was partly evaporated at room temperature from the covering and then the assembly placed to 110° C. for 2 hours. The result was a tough, dry, flexible hydrogel layer over a metal core. The thickness of the layer was 0.005", measured on a radius. The hydrogel was then treated in a Sulfuric acid, diluted with 30% of Glycerol for 30 seconds at 40° C., creating a sharp gradient of swelling and a low surface friction in contact with other materials.

What is claimed is:

1. A guidewire for insertion of tubular instruments into a body, which comprises:
   (a) a core element having sufficient rigidity to be inserted into a body;
   (b) an outside tubular layer about said core element, forming an elastomeric hydrogel sleeve, said sleeve having;
      (i) a chemical composition gradient with increasing concentration of polar groups in the outward direction away from said core element;
      (ii) a swelling gradient represented by increasing water content volumetrically in the outward direction away from said core element; and,
      (iii) compression stress decreasing the swelling at least in the outer most layer below its equilibrium value.

2. The guidewire of claim 1, wherein said hydrogel sleeve further includes an inwardly directed radial stress securing said outside tubular layer to said core element.

3. The guidewire of claim 1, wherein said core element is made of one or more materials selected from the group consisting of metal, plastic, carbon, glass and ceramics.

4. The guidewire of claim 1, wherein the core element has a substantially cylindrical cross section.

5. The guidewire of claim 1, wherein said elastomeric hydrogel sleeve is formed of a material selected from the group consisting of hydrophilic derivatives of acrylic acid, hydrophilic derivatives of methacrylic acid, and crosslinked hydrophilic polyvinylic compounds.

6. The guidewire of claim 1, wherein said elastomeric hydrogel sleeve is formed of hydrophilic polyurethanes or hydrophilic modified polyacrylonitriles.

7. The guidewire of claim 1, wherein said polar groups are selected from ionic groups consisting of carboxylic, sulfuric or sulfate groups.

8. The guidewire of claim 1, wherein said swelling gradient includes a water concentration of said tubular layer near its inner surface of about 25% to about 50% of water by volume, and at least about 90% of water by volume near its outer surface.

9. The guidewire of claim 1, wherein said tubular layer has a water concentration of at least about 95% by volume.

10. The guidewire of claim 1, wherein said tubular layer has a thickness of about 0.001 inches to about 0.1 inches.

11. A method of making a guidewire for insertion of tubular instruments into a body, which comprises:
   (a) by conventional methods, forming a core element having sufficient ridigity to be inserted into a body, from one or more materials selected from the group consisting of metal, plastic, carbon, glass and ceramics;
   (b) forming an outside tubular layer about said core as an elastomeric hydrogel sleeve, and controlling the formation of the elastomeric hydrogel sleeve to create:
      (i) a chemical composition gradient with increasing concentration of polar groups in the outward direction away from said core element; and,
      (ii) a swelling gradient represented by increasing water content volumetrically in the outward direction away from said core element.

12. The method of claim 11, wherein said hydrogel sleeve further includes an inwardly directed radial stress securing said outside tubular layer to said core element.

13. The method of claim 11, wherein said outside tubular layer is formed by melt extrusion.

14. The method of claim 13, wherein said extrusion is followed by the step of chemical modification by exposing the outer surface to a reagent to create said chemical composition gradient and said swelling gradient.

15. The method of claim 14, wherein said chemical modification increases concentration of hydrophilic groups.

16. The method of claim 14, wherein said chemical modification increases concentration of ionic groups.

17. The method of claim 14, wherein said chemical modification is under such condition that it is diffusion controlled.

18. The method of claim 13, wherein said hydrogel is derived from hydrophilic urethanes.

19. The method of claim 13, wherein said hydrogel is derived from modified polyacrylonitriles.

20. The method of claim 13, wherein said polar groups are selected from ionic groups consisting of carboxylic, sulfuric or sulfate groups.

21. The method of claim 11, wherein said elastomeric hydrogel sleeve is formed of a material selected from the group consisting of hydrophilic derivatives of acrylic acid hydrophilic derivatives of methacrylic acid, and crosslinked hydrophilic polyvinylic compounds.

22. The method of claim 11, wherein said outside tubular layer is formed by coagulation from solution.

23. The method of claim 21, wherein said coagulation from solution is followed by the step of chemical modification to create said chemical composition gradient and said swelling gradient.

24. The method of claim 22, wherein said hydrogel is derived from hydrophilic urethanes.

25. The method of claim 22, wherein said hydrogel is derived from modified polyacrylonitriles.

26. The method of claim 22, wherein said polar groups are selected from ionic groups consisting of carboxylic, sulfuric or sulfate groups.

27. The method of claim 11, wherein said outside tubular layer is formed by in situ polymerization.

28. The method of claim 27, wherein said hydrogel is derived from hydrophilic urethanes.

29. The method of claim 23, wherein said hydrogel is derived from modified polyacrylonitriles.

30. The method of claim 27, wherein said polar groups are selected from ionic groups consisting of carboxylic, sulfuric or sulfate groups.

31. The method of claim 11, wherein said polar groups are selected from ionic groups consisting of carboxylic, sulfuric or sulfate groups.

* * * * *